(12) United States Patent
Salvadori et al.

(10) Patent No.: US 7,462,171 B2
(45) Date of Patent: Dec. 9, 2008

(54) URINE COLLECTION BAG WITH ANGLED VALVE SUPPORT

(75) Inventors: Lawrence Salvadori, San Diego, CA (US); Ryan Stapleton, Medway, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 11/362,658

(22) Filed: Feb. 24, 2006

(65) Prior Publication Data
US 2007/0203465 A1   Aug. 30, 2007

(51) Int. Cl.
*A61M 1/00* (2006.01)
(52) U.S. Cl. .................. 604/327; 604/317; 604/540
(58) Field of Classification Search ......... 604/327–330, 604/332, 346–347, 349, 649
See application file for complete search history.

(56) References Cited

U.S. PATENT DOCUMENTS

| | | |
|---|---|---|
| 693,127 A | 2/1902 | Gardner et al. |
| 1,951,196 A | 3/1934 | Medows et al. |
| 2,630,303 A | 3/1953 | Krucker |
| 3,259,920 A | 7/1966 | Voller |
| 3,312,221 A | 4/1967 | Overment |
| 3,529,599 A | 9/1970 | Folkman et al. |
| 3,534,738 A | 10/1970 | Huck |
| 3,537,109 A | 11/1970 | Spurrier et al. |
| 3,537,455 A | 11/1970 | Skyles et al. |
| 3,583,401 A | 6/1971 | Vaillancourt |
| 3,601,119 A | 8/1971 | Engelsher |
| 3,650,272 A | 3/1972 | Ericson |
| 3,661,143 A | 5/1972 | Henkin |
| 3,661,153 A | 5/1972 | Polk et al. |
| 3,683,894 A | 8/1972 | Villari |
| 3,699,964 A | 10/1972 | Ericson |
| 3,716,055 A | 2/1973 | Schultze |
| 3,776,231 A | 12/1973 | Holbrook et al. |
| 3,800,795 A | 4/1974 | Walker |
| 3,820,546 A | 6/1974 | Chittenden et al. |
| 3,831,453 A | 8/1974 | McWhorter |
| 3,838,691 A | 10/1974 | Paludan et al. |
| 3,888,236 A | 6/1975 | Marx |
| 3,896,718 A | 7/1975 | Giambalvo |
| 3,906,930 A | 9/1975 | Raia et al. |
| 3,943,929 A | 3/1976 | Patel |
| 3,952,729 A | 4/1976 | Libman et al. |
| 3,961,529 A | 6/1976 | Hanifl |
| 4,000,649 A | 1/1977 | Hanifl |
| 4,002,075 A | 1/1977 | Cross |
| 4,013,064 A | 3/1977 | Patel et al. |
| 4,014,322 A | 3/1977 | Shah |

(Continued)

*Primary Examiner*—Michele Kidwell
(74) *Attorney, Agent, or Firm*—William E. Dee, Esq.

(57) ABSTRACT

A urine collection bag is provided which includes at least one sheet of flexible material defining a collapsible fluid reservoir and a support member defining a fluid channel and including a spout having an outlet opening. The support member is configured such that the longitudinal axis of the spout defines an acute angle with a horizontal axis when the fluid reservoir is empty but moves to a position wherein the longitudinal axis of the spout is substantially parallel to a vertical axis when the fluid reservoir is filled. The support member is configured to support a discharge valve such that the discharge valve is more accessible when the fluid reservoir is filled with fluid.

10 Claims, 7 Drawing Sheets

U.S. PATENT DOCUMENTS

| | | |
|---|---|---|
| 4,015,605 A | 4/1977 | McWhorter |
| 4,019,707 A | 4/1977 | Quinn et al. |
| 4,027,842 A | 6/1977 | Mittleman |
| 4,055,187 A | 10/1977 | Patel et al. |
| 4,085,616 A | 4/1978 | Patel et al. |
| 4,085,755 A | 4/1978 | Burrage |
| 4,095,589 A | 6/1978 | Manschot et al. |
| 4,100,802 A | 7/1978 | Layton |
| 4,105,500 A | 8/1978 | Libman et al. |
| 4,106,675 A | 8/1978 | Taylor |
| 4,109,837 A | 8/1978 | Taylor |
| 4,131,016 A | 12/1978 | Layton |
| 4,176,412 A | 12/1979 | Peterson |
| 4,178,934 A | 12/1979 | Forman |
| 4,187,722 A | 2/1980 | Layton |
| 4,189,789 A | 2/1980 | Hofstetter |
| 4,192,295 A | 3/1980 | Sherlock |
| 4,200,112 A | 4/1980 | McWhorter |
| 4,219,177 A | 8/1980 | O'Day |
| 4,238,448 A | 12/1980 | Salvador et al. |
| 4,241,017 A | 12/1980 | Balistreri |
| 4,254,771 A | 3/1981 | Vidal |
| 4,265,243 A | 5/1981 | Taylor |
| 4,280,498 A | 7/1981 | Jensen |
| 4,301,813 A | 11/1981 | Merry et al. |
| 4,305,290 A | 12/1981 | Taylor |
| 4,305,403 A | 12/1981 | Dunn |
| 4,305,404 A | 12/1981 | Dunn |
| 4,305,405 A | 12/1981 | Meisch |
| 4,312,351 A | 1/1982 | Kurtz et al. |
| 4,312,352 A | 1/1982 | Meisch et al. |
| 4,313,447 A | 2/1982 | Peterson et al. |
| 4,317,550 A | 3/1982 | Hannah |
| 4,328,828 A | 5/1982 | Cianci |
| 4,332,252 A | 6/1982 | Taylor |
| 4,333,480 A | 6/1982 | Villari et al. |
| 4,334,537 A | 6/1982 | Peterson |
| 4,344,432 A | 8/1982 | Pankau |
| 4,366,836 A | 1/1983 | Villari |
| 4,372,313 A | 2/1983 | Villari et al. |
| 4,384,485 A | 5/1983 | Layton et al. |
| 4,386,930 A | 6/1983 | Cianci |
| 4,393,880 A | 7/1983 | Taylor |
| 4,417,891 A | 11/1983 | Cianci |
| 4,417,892 A | 11/1983 | Meisch |
| 4,421,509 A | 12/1983 | Schneider et al. |
| 4,436,024 A | 3/1984 | Arden et al. |
| 4,447,939 A | 5/1984 | Taylor |
| 4,449,969 A | 5/1984 | Schweizer |
| 4,450,936 A | 5/1984 | Strom |
| 4,452,253 A | 6/1984 | Peterson et al. |
| 4,460,362 A | 7/1984 | Bates |
| 4,462,510 A | 7/1984 | Steer et al. |
| 4,465,479 A | 8/1984 | Meisch |
| 4,465,484 A | 8/1984 | Cianci |
| 4,475,907 A | 10/1984 | Voges |
| 4,483,688 A | 11/1984 | Akiyama |
| 4,490,144 A | 12/1984 | Steigerwald |
| 4,501,584 A | 2/1985 | Cianci et al. |
| 4,503,864 A | 3/1985 | Powers |
| 4,511,357 A | 4/1985 | Steigerwald |
| 4,511,358 A | 4/1985 | Johnson, Jr. et al. |
| 4,512,770 A | 4/1985 | Cianci et al. |
| 4,521,213 A | 6/1985 | Steigerwald |
| 4,526,576 A | 7/1985 | Cianci |
| 4,529,398 A | 7/1985 | Wong et al. |
| 4,534,766 A | 8/1985 | Steer et al. |
| 4,551,141 A | 11/1985 | McNeil |
| 4,562,984 A | 1/1986 | Sherlock et al. |
| 4,564,361 A | 1/1986 | Akiyama |
| 4,573,983 A | 3/1986 | Annis |
| 4,579,126 A | 4/1986 | Cianci |
| 4,581,763 A | 4/1986 | Olsen |
| 4,604,092 A | 8/1986 | Silver |
| 4,604,095 A | 8/1986 | Samuelsen |
| 4,606,420 A | 8/1986 | Silver |
| 4,606,736 A | 8/1986 | Van De Weghe |
| 4,619,648 A | 10/1986 | Rath et al. |
| 4,622,981 A | 11/1986 | Sherlock |
| 4,625,734 A | 12/1986 | Sherlock et al. |
| 4,631,056 A | 12/1986 | Dye |
| 4,633,887 A | 1/1987 | Edwards et al. |
| 4,634,437 A | 1/1987 | Lowthian |
| 4,640,128 A | 2/1987 | Lewis |
| 4,642,105 A | 2/1987 | Toter |
| 4,650,478 A | 3/1987 | Dunn |
| 4,658,834 A | 4/1987 | Blankenship et al. |
| 4,659,329 A | 4/1987 | Annis |
| 4,660,802 A * | 4/1987 | Oscarsson .................. 251/9 |
| 4,661,100 A | 4/1987 | Rechsteiner |
| 4,691,557 A | 9/1987 | Dunn et al. |
| 4,693,707 A | 9/1987 | Dye |
| 4,693,712 A | 9/1987 | Bates |
| 4,699,155 A | 10/1987 | Villari et al. |
| 4,700,714 A | 10/1987 | Fuisz |
| 4,702,740 A | 10/1987 | Bates |
| 4,717,388 A | 1/1988 | Steer et al. |
| 4,723,944 A | 2/1988 | Jensen |
| 4,723,950 A | 2/1988 | Lee |
| 4,728,324 A | 3/1988 | Steigerwald et al. |
| 4,731,062 A | 3/1988 | Gross et al. |
| 4,738,671 A | 4/1988 | Elliott et al. |
| 4,743,236 A | 5/1988 | Manschot |
| 4,745,929 A | 5/1988 | Silver |
| 4,753,249 A | 6/1988 | Muller |
| 4,790,837 A | 12/1988 | Gross et al. |
| 4,804,376 A | 2/1989 | Layton |
| 4,815,477 A | 3/1989 | McWhorter et al. |
| 4,838,876 A | 6/1989 | Wong et al. |
| 4,850,375 A | 7/1989 | Rosenberg |
| D303,714 S | 9/1989 | Manschot |
| 4,865,046 A | 9/1989 | Duran |
| 4,909,478 A | 3/1990 | Steer |
| 4,911,697 A | 3/1990 | Kerwin |
| 4,913,161 A | 4/1990 | Villari et al. |
| 4,936,837 A | 6/1990 | Wexler et al. |
| 4,946,451 A | 8/1990 | Cianci |
| 4,955,879 A | 9/1990 | Mervine |
| 4,972,844 A | 11/1990 | Cianci et al. |
| 5,026,359 A | 6/1991 | Burroughs |
| 5,098,418 A | 3/1992 | Maitz et al. |
| 5,116,139 A | 5/1992 | Young et al. |
| 5,119,675 A | 6/1992 | Mohiuddin |
| 5,160,329 A | 11/1992 | Oxley |
| 5,207,661 A | 5/1993 | Repschlager |
| 5,211,642 A | 5/1993 | Clendenning |
| 5,217,443 A | 6/1993 | Oxley |
| 5,300,050 A | 4/1994 | Everett, Jr. et al. |
| 5,312,379 A | 5/1994 | Rahe |
| 5,354,132 A | 10/1994 | Young et al. |
| 5,356,398 A | 10/1994 | Willis |
| 5,368,583 A | 11/1994 | Fleury |
| 5,409,014 A | 4/1995 | Napoli et al. |
| 5,417,657 A | 5/1995 | Hauer |
| 5,423,792 A | 6/1995 | Oxley |
| 5,429,624 A | 7/1995 | Coelho, Jr. |
| 5,439,456 A | 8/1995 | Fabricant |
| 5,466,229 A | 11/1995 | Elson et al. |
| 5,489,281 A | 2/1996 | Watanabe et al. |
| 5,507,734 A | 4/1996 | Everett, Jr. et al. |
| 5,523,055 A | 6/1996 | Hansen et al. |
| 5,569,225 A | 10/1996 | Fleury |
| 5,616,138 A | 4/1997 | Propp |
| 5,662,630 A | 9/1997 | Raynie |

| | | | | | |
|---|---|---|---|---|---|
| 5,725,515 A | 3/1998 | Propp | 6,409,131 B1 | 6/2002 | Bentley et al. |
| 5,792,127 A | 8/1998 | Marran | 6,409,971 B1 | 6/2002 | Wilkinson et al. |
| 5,891,051 A | 4/1999 | Han et al. | 6,551,292 B1 | 4/2003 | D'Acchioli et al. |
| 5,919,146 A | 7/1999 | Propp | 6,582,379 B1 | 6/2003 | Stisen |
| 5,961,501 A | 10/1999 | Cassidy et al. | 6,635,036 B1 | 10/2003 | Tanghoej et al. |
| 5,989,234 A | 11/1999 | Valerio et al. | 6,709,420 B1 * | 3/2004 | Lincoln et al. .............. 604/323 |
| 6,129,684 A | 10/2000 | Sippel et al. | 6,736,803 B2 | 5/2004 | Cawood |
| 6,129,714 A | 10/2000 | Kocsi | 6,793,651 B1 | 9/2004 | Bennett et al. |
| 6,210,383 B1 | 4/2001 | Want et al. | D496,993 S | 10/2004 | Kubalack et al. |
| 6,250,482 B1 | 6/2001 | Want et al. | D497,205 S | 10/2004 | Kubalack et al. |
| 6,338,728 B1 | 1/2002 | Valerio | | | |

* cited by examiner

URINE COLLECTION BAG WITH ANGLED VALVE SUPPORT

BACKGROUND

1. Technical Field

The present disclosure relates to fluid collection bags for receiving bodily fluids, e.g., urine. More specifically, the present disclosure relates to a collapsible urine collection bag including an angled support member for mounting a discharge valve thereon defining a fluid channel and having a spout. The support member is configured to position the discharge valve and the spout are in a more accessible and proper orientation to effect spill free drainage of the bag when the bag is filled or partially filled with fluid.

2. Background of Related Art

Fluid collection systems for collecting bodily fluids such as urine are well known in the art. Typically, urine collection systems include a urine collection bag defining a fluid reservoir and having an inlet port or ports for receiving fluid and a discharge port to facilitate drainage of the collection bag. A discharge tube is attached to the discharge port and a discharge valve is provided on or along the discharge tube to regulate fluid flow, e.g., drainage, from the collection bag.

Generally, a fluid collection bag is formed from front and rear sheets of flexible material sealed together at their edges to define a fluid reservoir. A discharge port is positioned on a lower end of the front sheet of the collection bag with a discharge tube extending therefrom. In some known collection systems, a discharge valve is supported on the discharge tube or mounting structure supported on the bag at a location to regulate fluid flow through the discharge tube.

In use, a urine collection bag is supported, e.g., hung, on support structure, e.g., a bed frame, located below a patient. A drain tube having one end connected to a catheterized patient and a second end in fluid communication with the urine collection bag directs urine to the urine collection bag. When the urine collection bag begins to fill, the front and rear sheets forming the collection bag expand outwardly. Since the lower end of the front and rear sheets are sealed together, the lower end of the front sheet of the collection bag expands such that the exterior surface of the collection bag defines a curved downwardly facing surface. This outward bulging of the front sheet of the collection bag, causes a discharge spout of the collection bag and the discharge valve to tilt inwardly. As a result, the discharge valve becomes less accessible and the discharge spout moves to skewed on non-vertical orientation to make spill free drainage of the collection bag.

Accordingly, it would be desirable to provide a collection bag having mounting structure for the discharge valve which compensates for expansion of a fluid collection bag to facilitate rapid and spill free drainage of the fluid collection bag.

SUMMARY

In accordance with the present disclosure, a urine collection bag is provided which includes a first sheet of flexible material and a second sheet of flexible material secured together to define a collapsible fluid reservoir. The first sheet of flexible material defines an opening to facilitate drainage of the reservoir.

A support member defines a fluid channel and includes a spout defining a longitudinal axis and a fluid outlet. The support member is secured to the first sheet of flexible material such that the fluid channel is in fluid communication with the opening in the first sheet of flexible material. The support member is configured such that the longitudinal axis of the spout and a horizontal axis define an angle β when the fluid reservoir of the collection bag is empty, wherein β is between about 15° and about 75°.

In a preferred embodiment β is between about 30° and about 60°. In another preferred embodiment, is about 45°.

In one embodiment, the support member includes a base portion defining an inlet opening and a central body portion. The fluid channel extends from the base portion through the central body portion to the spout. The central body portion defines a longitudinal axis which is substantially parallel to a horizontal axis when the fluid reservoir of the urine collection bag is empty. The base portion is a plate-like member which can be welded to the front sheet of flexible material.

The urine collection bag further includes a discharge valve supported on the support member and a flexible discharge tube secured to the spout of the support member. The discharge valve includes a housing and a rotatable valve member. The rotatable valve member is movable from a closed position compressing the flexible discharge tube to an open position to permit fluid to flow through the discharge tube.

BRIEF DESCRIPTION OF THE DRAWINGS

Various embodiments of the presently disclosed fluid collection bag with angled valve support member are disclosed herein with reference to the drawings, wherein.

DETAILED DESCRIPTION OF EMBODIMENTS

Figure 1:
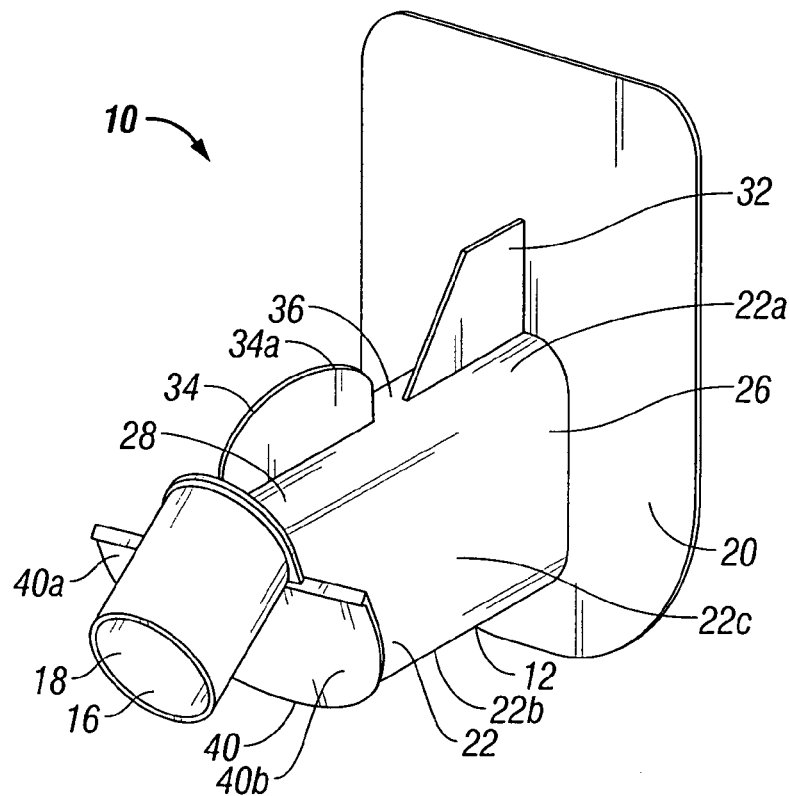
FIG. 1 is a perspective view of one embodiment of the presently disclosed valve support member of a fluid collection bag.

Embodiments of the presently disclosed urine collection bag assembly with angled valve support member will now be described in detail with reference to the drawings wherein like reference numerals designate identical or corresponding elements in each of the several views.

Figure 6:
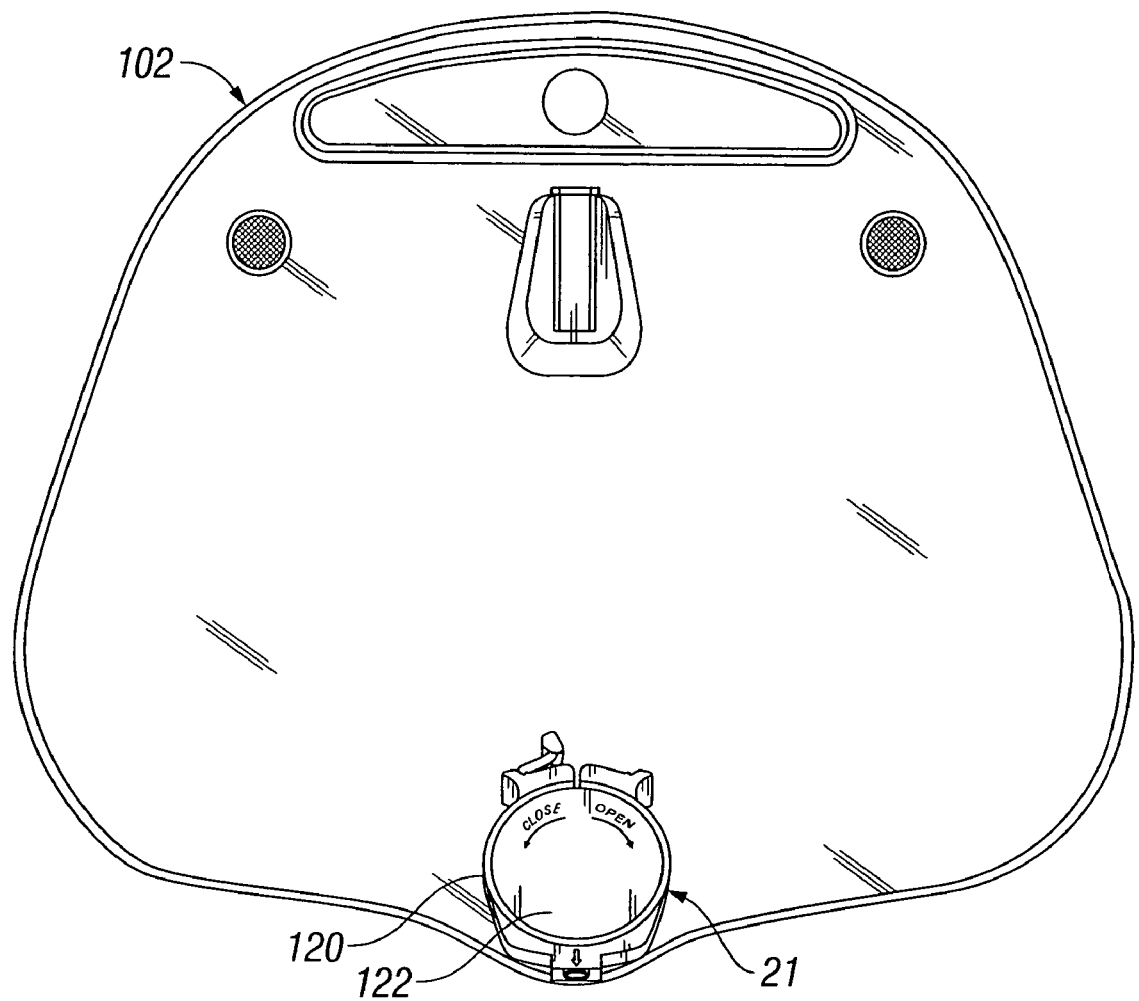
FIG. 6 is a front view of the fluid collection bag shown in FIG. 5 with a discharge valve supported on the valve support member.

FIGS. 1-4 illustrate a valve support member 10 for supporting a fluid discharge valve 21 (FIG. 6). Valve support member 10 is configured for use with a urine collection bag assembly 100 (FIG. 10) and includes a body 12 defining a fluid inlet 14 (FIG. 4), a fluid outlet 16 (FIG. 1), and a fluid channel 18 extending between fluid inlet 14 and fluid outlet 16. Body 12 of valve support member 10 includes a base member 20 through which fluid inlet 14 extends, a central body portion 22 which defines a substantial portion of fluid channel 18 and a spout 24. Spout 24 defines the outlet end of fluid channel 18 including fluid outlet 16.

Figure 2:
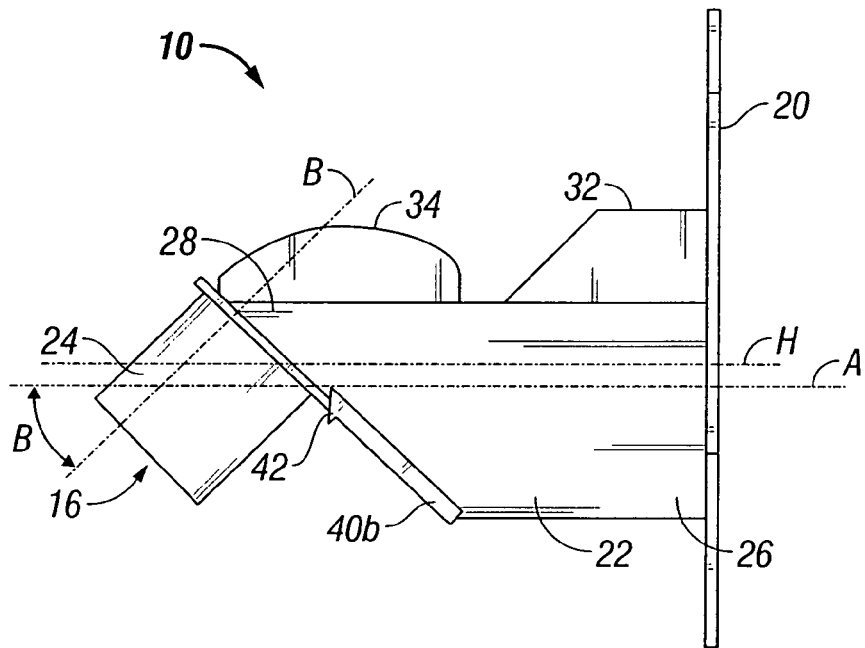
FIG. 2 is a side view of the valve support member shown in FIG. 1.
Figure 3:
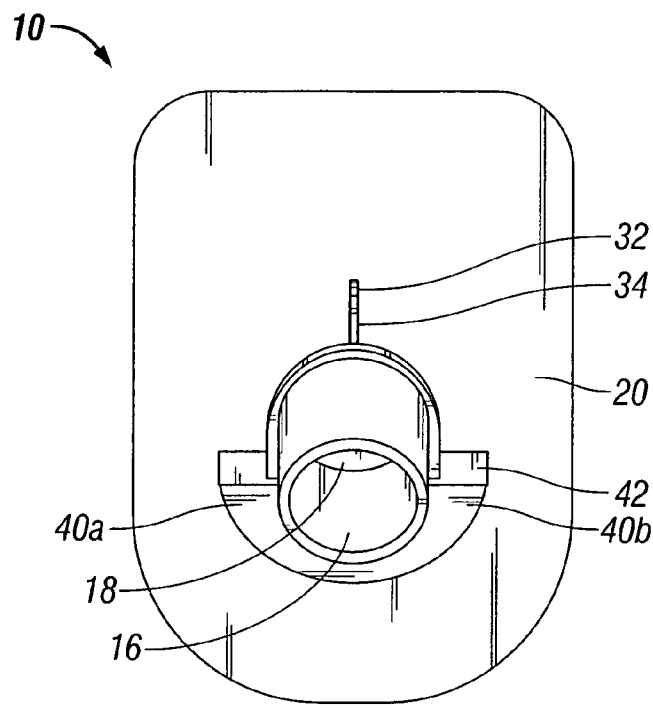
FIG. 3 is a front view of the valve support member shown in FIG. 1.
Figure 4:
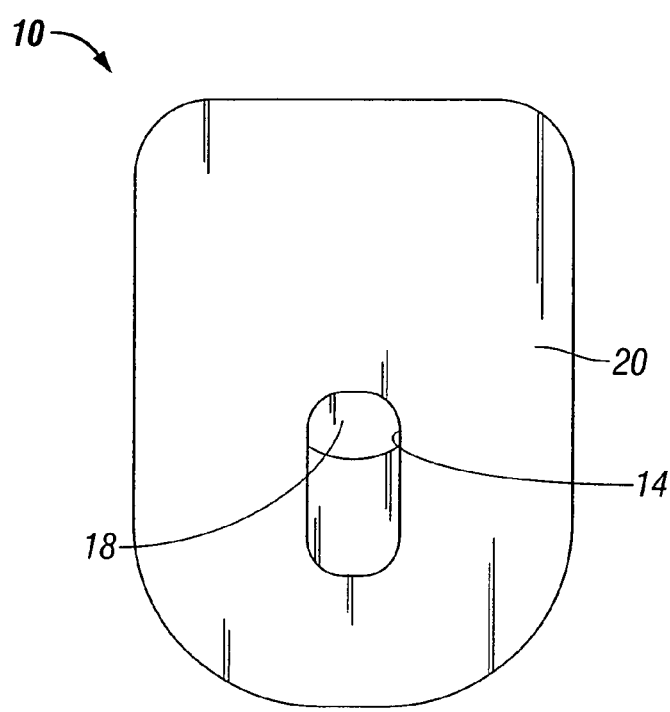
FIG. 4 is a rear view of the valve support member shown in FIG. 1.

Support member 10 can be monolithically constructed from a polymeric material or any other material having the requisite strength characteristic. Alternately, the components of support member 10 can be constructed from different materials and fastened together using any known fastening process, e.g., welding, adhesives, etc. In one embodiment, base member 20 defines a flat, plate-like member which is configured to being sealingly attached to collection bag 102 as will be discussed in further detail below. As shown in FIGS. 1 and 2, central body portion 22 is substantially rectangular in shape and includes rounded top and bottom surfaces 22a and 22b and linear sidewalls 22c. Alternately, other body portion configurations are envisioned, e.g., square, cylindrical, oval, etc. Central body portion 22 defines a longitudinal axis "A" which is substantially parallel to a horizontal axis "H" when the collection bag is empty (FIG. 2). Central body portion 22 has a first end 26 formed integrally with or fastened to base member 20 and a second end 28 spaced from base member 20. Spout 24 defines a second longitudinal axis "B" and is supported on second end 28 of central body portion 22. Spout 24 has a substantially cylindrical configuration although other configurations are envisioned. In one embodiment, first and second longitudinal axis A and B define an angle β of between about 15° and about 75° and preferably between about 30° and about 60°. In one embodiment, β is about 45°. It is envisioned that other angles may be desirable outside of the ranges listed above, e.g., 10°, etc. As discussed above, a fluid channel 18 extends through support member 10 from fluid inlet 14 (FIG. 4) to fluid outlet 16. Angle β is chosen such that when collection bag 102 is filled with fluid and the outer wall of bag 102 bulges outwardly, the longitudinal axis 13 of spout 24 moves to a substantially vertical orientation.

Support member 10 also includes a strut 32 which is supported on an upper surface of first end 26 of central portion 22 and includes a first edge fastened to central portion 22 and a second edge fastened to a front surface of base member 20. Strut 32 is substantially rigid and provides stability to support member 10. A fin 34 is supported on second end 28 of central portion 22. In one embodiment, fin 34 includes a curved upper surface 34a and is configured to be positioned within discharge valve 21 to assist in securing discharge valve 21 to support member 10. Fin 34 and strut 32 are spaced on central body portion 22 to define a recess 36.

A flange or support plate 40 is secured to second end 28 of central body portion 22 below spout 24. Support plate 40 includes first and second transverse extensions 40a and 40b defining an engagement surface 42. One end of plate 40 has a lip or overhang 41. Engagement surface 42 defines a plane which is substantially perpendicular to second longitudinal axis B. Transverse extensions 40a and 40b and engagement surface 42 in combination with fin 34 facilitate attachment of support member 10 to discharge valve 21 as will be discussed in detail below.

Figure 10:
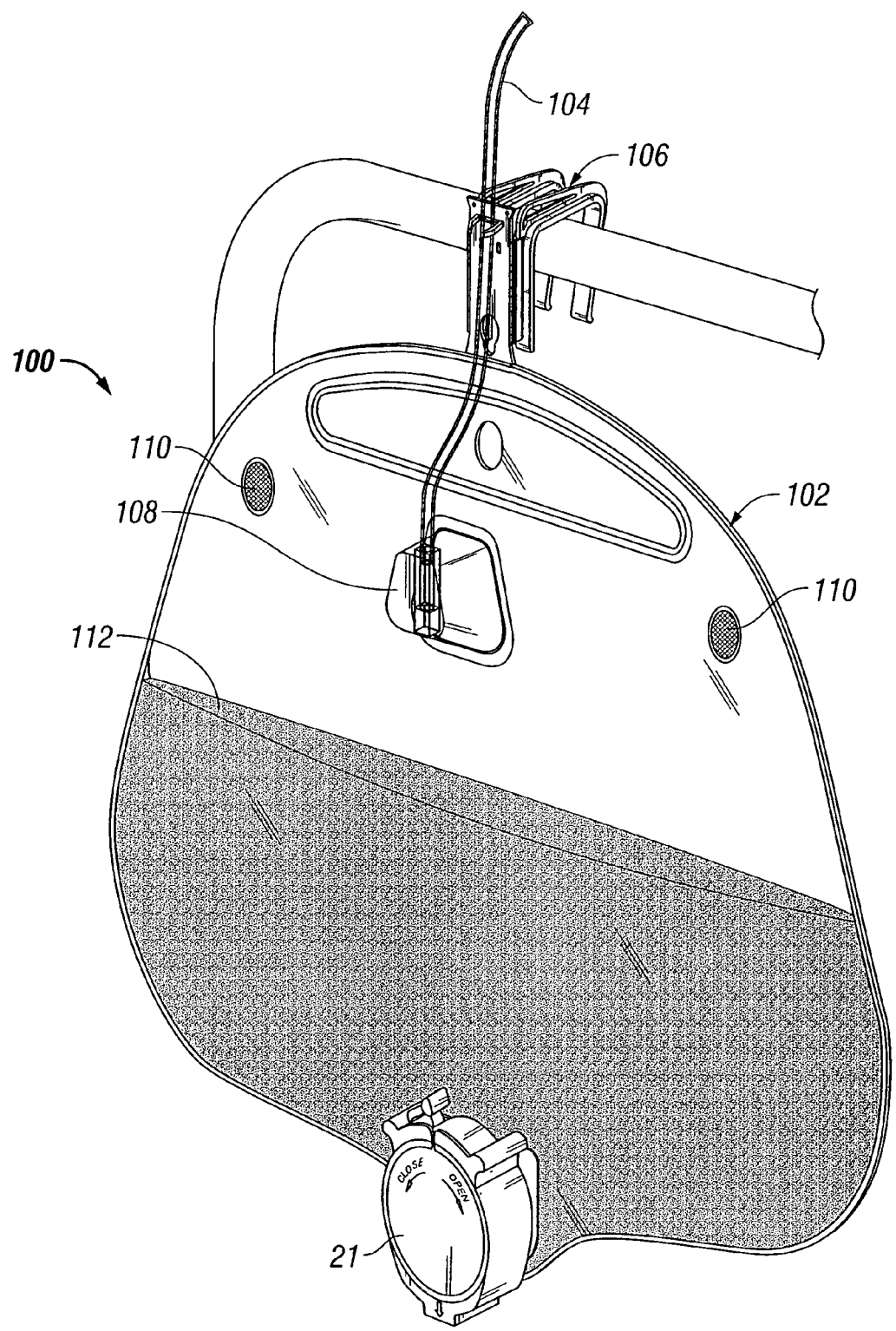

Referring briefly to FIG. 10, collection bag assembly 100 includes collection bag 102 including discharge valve 21, a drain tube 104 and a support hangar 106. Collection bag 102 also can include an inlet or anti-reflux valve 108 and one or more vents 110. As illustrated, discharge valve 21 is supported adjacent a bottom portion of bag 102

Figure 5:
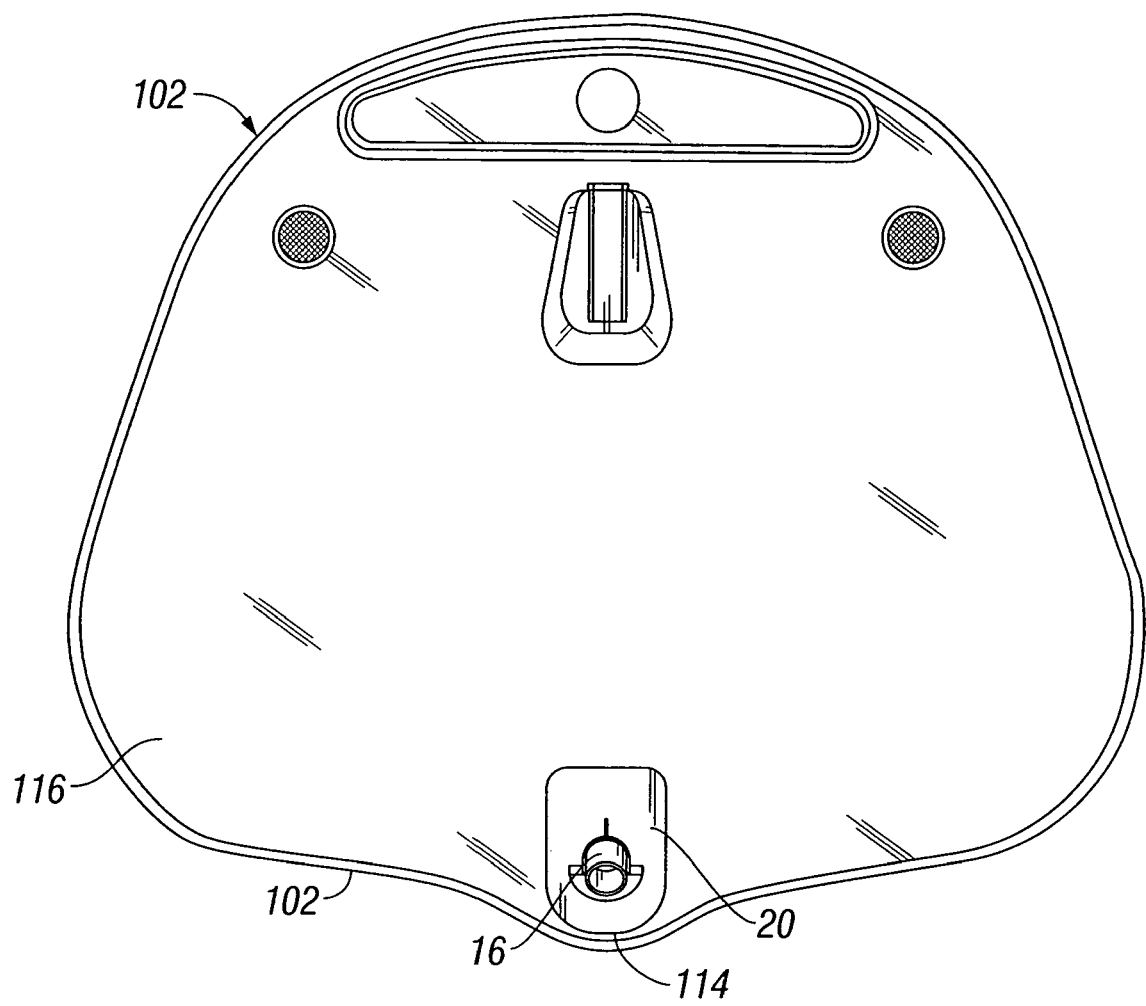
FIG. 5 is a front view of a fluid collection bag having the valve support member shown in FIG. 1 secured thereto.

Referring to FIGS. 5 and 10, collection bag 102 is constructed from first and second sheets of flexible material which are sealed, e.g., welded, glued, etc. at their edges to define a fluid reservoir 112 (FIG. 10). The first and second sheets of material may be constructed from polyvinyl chloride or other suitable flexible material. The bottom portion of collection bag 102 defines a gulley or well 114 which defines the lowest point of fluid reservoir 112. An opening (not shown) is formed in first sheet 116 of collection bag 102. Base member 20 of support member 10 is secured to first sheet 116 using any known fastening technique, e.g., heat sealing, adhesives, welding, etc., such that fluid inlet 14 (FIG. 4) is in fluid communication with the opening in front sheet 116 of collection bag 102 and central portion 22 of support member 10 projects outwardly from front sheet 116 of collection bag 102. A flexible discharge tube 117 is secured to spout 24 and extends through discharge valve 21. As such, fluid in collection bag 102 collects in the bottom of collection bag 102 and flows through the opening in front sheet 116 into fluid channel 18 of support member 10 and into discharge tube 117.

Figure 7:
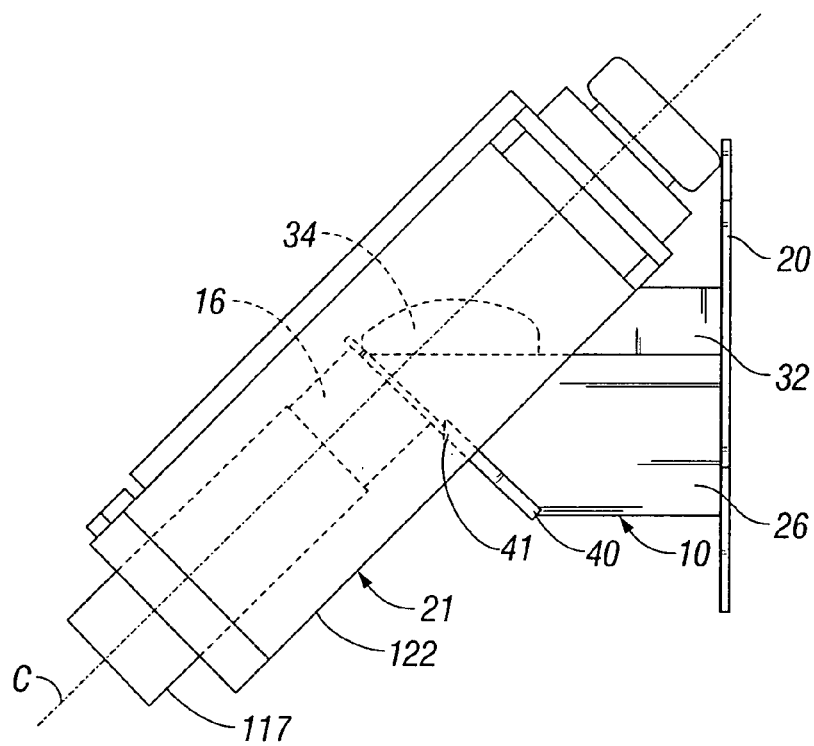
FIG. 7 is a side perspective view of the fluid collection bag shown in FIG. 6 including a drain tube and hangar structure for securing the collection bag on a bed frame.
Figure 8:
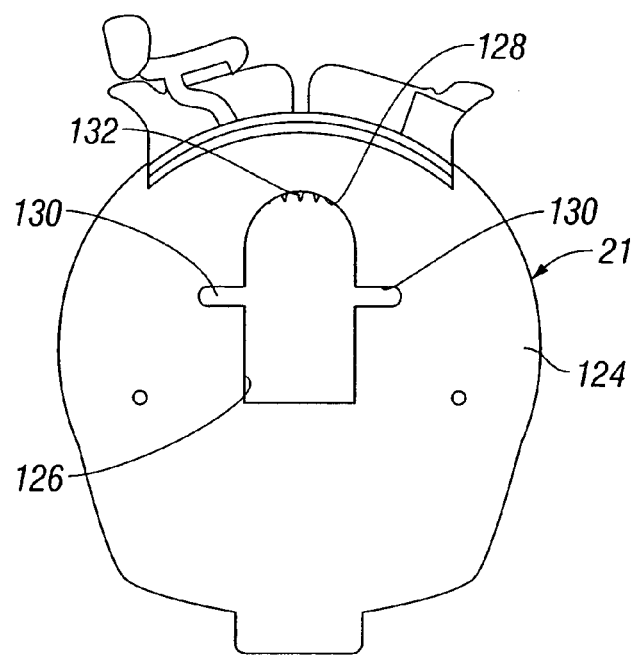
FIG. 8 is a side perspective view of the collection bag assembly shown in FIG. 7 with the collection bag partially filled with fluid.

Referring to FIGS. 6-8, discharge valve 21 has an outer housing 120 and a rotatable valve member 122 positioned within and defining a front surface of discharge valve 21. Valve member 122 is movable from a first position compressing flexible tube 117 to a second position wherein substantially no compression is applied to tube 117 and fluid can flow from tube 117. Discharge valve 21 is known in the art and is sold by Kendall under the trade name SPLASHGUARD II™ and will not be discussed in specific detail herein. Alternately, other valve types may be used in conjunction with the presently disclosed support member. Outer housing 120 of valve 21 includes a rear wall 124 which includes an opening 126 (FIG. 8). In one embodiment, opening 126 is substantially rectangular and includes a circular upper wall 128 and a pair of linear transverse slots 130. A series of small spaced protrusions 132 project inwardly from upper wall 128. Protrusions 132 cooperate with fin 34 to align support member 12 within valve 21.

Opening 126 is dimensioned to receive a distal portion of body 12 of support member 10. More specifically, the portion of body 12 of support member 10 including spout 24 and the distal portion of central body portion 22 is inserted through opening 126 into outer housing 120 of discharge valve 21. In this position, fin 34 of support member 10 is positioned within outer housing 122 and transverse extensions 40a and 40b of support plate 40 extend through transverse slots 130 of opening 126 such that engagement surface 42 rests on the portion of outer housing 120 defining slots 130. With discharge valve 21 supported on support member 10, discharge valve 21 defines a longitudinal axis "C" which is parallel to axis B defined by spout 24 of support member 10 and offset by angle β from axis A defined by the central body portion 22 of support member 10.

Figure 9:
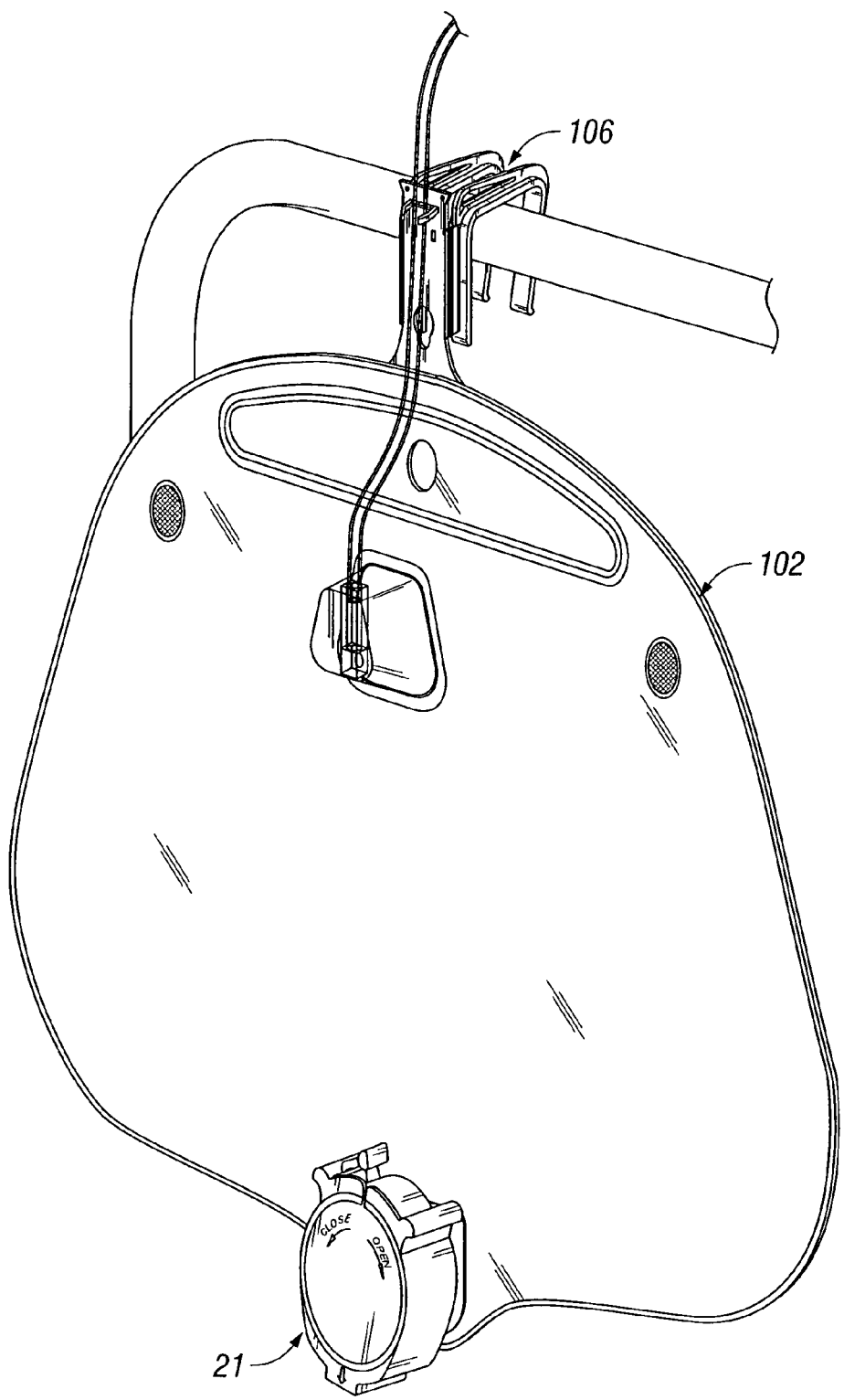

As illustrated in FIGS. 6, 7 and 9, base member 20 of support member 10 is secured to front sheet 116 of collection bag 102 and discharge valve 21 is supported on support member 10. Thus, when collection bag 102 is in its non-expanded or empty configuration, longitudinal axis B of spout 24 (FIG. 2) and longitudinal axis C of discharge valve 21 (FIG. 7) are tilted upwardly at an angle β from a horizontal axis or plane defined by front sheet 116 of collection bag 102. As collection bag 102 fills with fluid and front sheet 116 bulges outwardly, longitudinal axis B of spout 24 and longitudinal axis C of discharge valve 21 rotate back towards a vertical position (FIG. 9). Thus, as collection bag 102 fills and collection bag 102 bulges outwardly, spout 24 and discharge valve 21 move to a position in which rotatable valve member 122 is more easily accessible and fluid can be drained spill free from collection bag 102, i.e., spout 24 is moved to a vertical position in which fluid outlet 18 is able to drain straight downwardly.

It will be understood that various modifications may be made to the embodiments disclosed herein. For example, it is envisioned that the configuration of the support member may be altered in many respects to support a variety of different valve configurations. Such is considered within the scope of this disclosure so long as the configuration of the support member is selected to compensate for outward bulging of the urine collection bag. Further, the present disclosure may be incorporated into collection bags in other surgical and non-surgical areas. Therefore, the above description should not be construed as limiting, but merely as exemplifications of preferred embodiments. Those skilled in the art will envision other modifications within the scope and spirit of the claims appended hereto.

What is claimed is:

1. A urine collection bag comprising:
   a first sheet of flexible material and a second sheet of flexible material secured together to define a fluid reservoir, the first sheet of flexible material defining an opening to facilitate drainage of the reservoir; and
   a support member having a plate-like base member and a central body portion defining a fluid channel, the central body portion defining a longitudinal axis which is substantially perpendicular to a plane defined by the plate-like base member, the support member further including a spout defining a longitudinal axis and a fluid outlet, the central body portion having a first end defining a fluid inlet through the base member and a second end in fluid communication with the spout, the base member of the support member being secured to the first sheet of flexible material such that the fluid channel is in fluid communication with the opening in the first sheet of flexible material;
   wherein the support member is configured such that the longitudinal axis of the spout and the longitudinal axis of the central body portion of the support member define an angle β, wherein β is between about 15° and about 75°.

2. A urine collection bag according to claim 1, wherein β is between about 30° and about 60°.

3. A urine collection bag according to claim 2, wherein β is about 45°.

4. A urine collection bag according to claim 1, wherein the urine collection bag further includes a discharge valve supported on the support member.

5. A urine collection bag according to claim 4, further including a flexible discharge tube secured to the spout of the support member.

6. A urine collection bag according to claim 5, wherein the discharge valve includes a housing and a rotatable valve member, the rotatable valve member being movable from a closed position compressing the flexible discharge tube to an open position to permit fluid to flow through the discharge tube.

7. A urine collection bag according to claim 4, wherein the base member is welded to the first sheet of flexible material.

8. A fluid collection assembly comprising:
   a fluid collection bag including at least one sheet of material configured to define a reservoir including an aperture to facilitate the drainage thereof, the fluid collection bag being adapted to translate from a first position in which the reservoir is substantially empty to a second position in which the reservoir is at least partially full; and
   a support member including a base member secured to the fluid collection bag, the support member including a central body portion defining a fluid channel and having a longitudinal axis and, the support member further including a spout defining a fluid outlet and a longitudinal axis, the support member being secured to the fluid collection bag such that the fluid channel is in fluid communication with the aperture;
   wherein the longitudinal axis of the central body portion is substantially perpendicular to a plane defined by the base member and the longitudinal axis of the central body portion and the longitudinal axis of the spout define an angle β of between about 15° and about 75°, wherein the support member is configured such that in the second position of the fluid collection bag, the longitudinal axis of the spout is in a substantially vertical orientation.

9. The fluid collection assembly of claim 8, wherein the at least one sheet of material includes first and second sheets of flexible material secured together to define the reservoir therebetween, the first sheet of flexible material defining the aperture to facilitate drainage of the reservoir.

10. The fluid collection assembly of claim 8, wherein the longitudinal axis of the spout and a vertical axis define a first angle therebetween in the first position of the fluid collection bag and a second angle therebetween in the second position of the fluid collection bag, the second angle being about 0°.

* * * * *